United States Patent [19]

Peterson

[11] Patent Number: 4,685,326

[45] Date of Patent: Aug. 11, 1987

[54] RESONANT DETERMINATION OF SATURATION CHANGES IN ROCK SAMPLES

[75] Inventor: Paul E. Peterson, San Mateo, Calif.

[73] Assignee: Petrophysical Services, Inc., Mountain View, Calif.

[21] Appl. No.: 837,800

[22] Filed: Mar. 10, 1986

[51] Int. Cl.[4] .................. G01N 15/08; G01N 5/02
[52] U.S. Cl. ............................. 73/38; 73/580; 73/73
[58] Field of Search .......... 73/580, 73, 153, 38, 73/666, 668; 177/210 FP

[56] References Cited

U.S. PATENT DOCUMENTS

| | | | |
|---|---|---|---|
| 3,018,660 | 1/1962 | Schmid | 73/38 |
| 3,261,202 | 7/1966 | King | 73/73 |
| 3,555,886 | 1/1971 | Thornton | 73/666 |
| 4,405,024 | 9/1983 | Fraval et al. | 177/210 FP |
| 4,543,821 | 10/1985 | Davis | 73/38 |

Primary Examiner—John Chapman
Attorney, Agent, or Firm—Albert B. Kimball, Jr.; Robert E. Lowe

[57] ABSTRACT

Mass, or changes in mass, of a rock specimen are measured to determine the changes in saturation of a rock specimen. Measurements can be obtained in test environments of high temperature or high pressure or both. The mass is rigidly attached beneath a stiff spring and made to vibrate or oscillate at a characteristic frequency. The frequency of oscillation is detected and the data then used to determine mass of the specimen.

23 Claims, 2 Drawing Figures

U.S. Patent    Aug. 11, 1987    4,685,326

RESONANT DETERMINATION OF SATURATION CHANGES IN ROCK SAMPLES

BACKGROUND OF INVENTION

1. Field of Invention

The present invention relates to obtaining a measure of the saturation, i.e. the relative fluid content, of a rock specimen.

2. Description of Prior Art

It is helpful in analyzing subsurface formations of interest for possible hydrocarbon content to know the saturation of the formation. Core samples from the formations are obtained and used as test specimens. Where certain data as to specimen mass and geometry are known, the saturation of the rock may be determined. Changes in mass during testing are indicative, when measured, of changes in saturation.

So far as is known, there was no convenient way in terms of size or affordability to measure rock saturation. The prior art saturation testing of rock specimens has been done by any of several of what were known generally as gravimetric techniques. A common feature of these techniques was that they were difficult to perform when the rock specimen was undergoing testing at elevated temperatures or pressures, both of which are typically present in the formations from which the samples were taken.

SUMMARY OF INVENTION

Briefly, the present invention provides a new and improved apparatus and method for detecting changes in saturation of a rock sample. Saturation is a measure of the extent to which pore space in the rock sample either contains or can be made to contain or release fluids such as hydrocarbons or gases.

The rock sample is held in a suitable holder or container which is rigidly attached to a resilient spring. Excitation, either electromagnetic or mechanical, is applied to the rock holder. In response to the applied excitation, the rock sample oscillates at a frequency which is determined by the spring constant of the resilient spring and the mass of the rock sample. The oscillation of the rock sample is detected and from this measurement the mass of the rock sample is determined. During testing, the rock sample may be subjected to different pressure and temperature conditions and injected with different types of fluids, such as secondary or tertiary recovery liquids or gases. Oscillation of the rock sample may be detected magnetically, optically or acoustically. If the density of the fluid content of the rock sample changes, this will be indicated as a change in mass.

The excitation applied is typically at a frequency, either fundamental or harmonic, near that expected to occur due to the mass of the rock sample and the spring constant. In this way, signals representing the detected oscillation of the rock sample and applied excitation may be subjected to a phase comparison. Small changes in the phase or frequency of oscillation of the rock specimen which indicate slight changes in saturation can thus be detected.

DESCRIPTION OF PREFERRED EMBODIMENT

Figure 1:
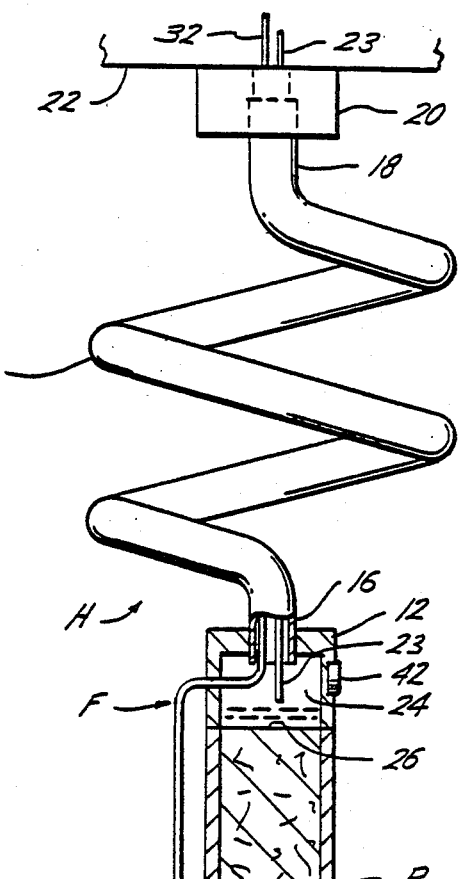
FIG. 1 is an elevation view, taken partially in cross-section, of an apparatus according to the present invention.
Figure 2:
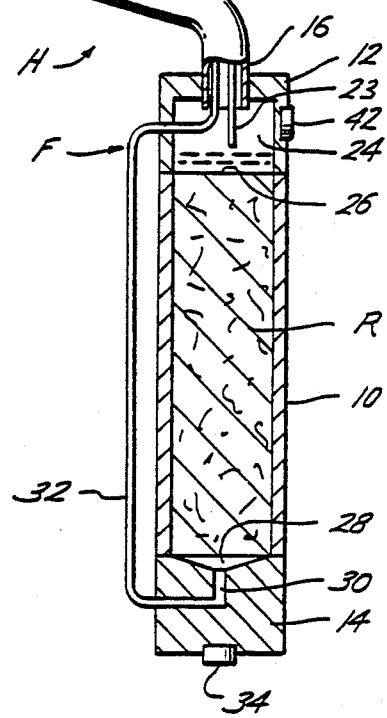
FIG. 2 is an elevation view, partially schematic, of a sample testing system according to the present invention using the apparatus of FIG. 1.
Figure 2:
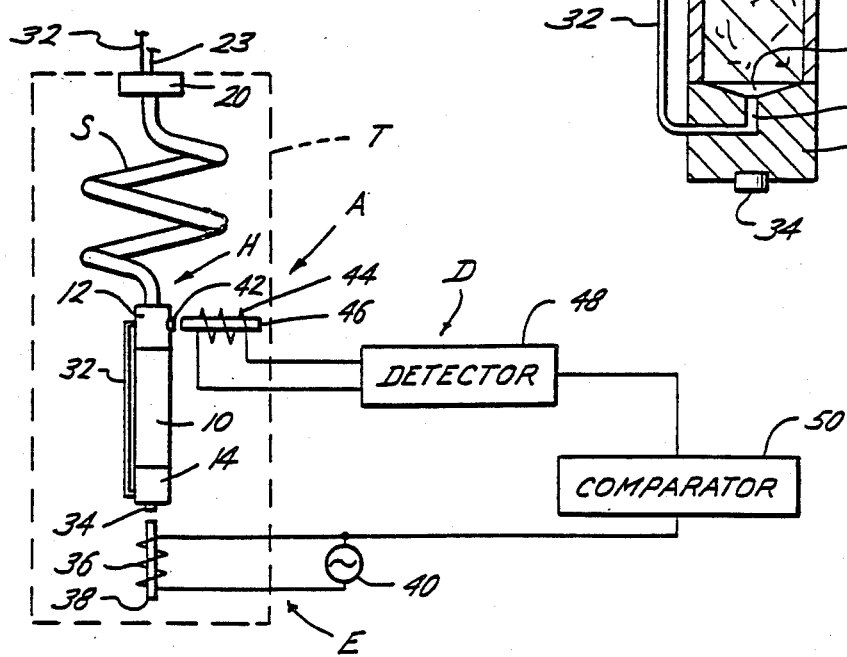

In the drawings, the letter A designates an apparatus for determining the saturation of a rock sample R to obtain a measure of its saturation, or the extent to which the pore space in the rock sample R can either be made to contain or release fluids such as hydrocarbons. The rock sample R is typically a cylindrical core sample obtained from a subsurface formation adjacent a well bore. Information as to the saturation of the rock sample R provides information useful in analyzing whether the formation from which the sample R was taken is of interest for petroleum production. The apparatus A includes a holding mechanism H which holds the rock sample R during testing and includes a resilient spring S which is rigidly attached to a wall of a test vessel T which may, for example, be a pressure vessel or high temperature oven. An excitation system E applies excitation to the holding mechanism A during testing so that a detector system D may detect oscillation of the rock sample R in response to the applied excitation.

The physical principle upon which the present invention is based is that of the behavior of a mass rigidly attached beneath a resilient spring, such as spring S. When excitation is applied to the mass, the mass oscillates upwardly and downwardly and the spring S is alternately compressed and expanded, correspondingly. If friction and damping losses are small and can effectively be disregarded, the frequency f at which the oscillatory motion of the mass m occurs can be generally adequately characterized as:

$$f = \sqrt{k/m} \qquad (1)$$

where k is the spring constant of the spring S and m is the mass of the test assembly including the rock sample R.

Although the holding mechanism H does have some mass and thus an effect on the frequency f, this mass will remain the same during a given test and will therefore not vary the frequency f. Thus, changes in the mass of the rock sample R, resulting from changes in density of its fluid content, are the principal factors which cause the frequency of oscillation the entire holding mechanism H to vary. During the testing, the sample R is subjected to different pressure and temperature conditions and injected with different types of fluids, such as secondary or tertiary recovery liquids or gases to evaluate the response of the rock sample R. Resulting changes in the frequency under varying test conditions are detected and provide useful information in analyzing behavior of subsurface formations of interest for possible hydrocarbon content or production capacity.

In the apparatus A, the rock sample R is fitted within a generally tubular sleeve or jacket member 10 of the holding mechanism H. The jacket mechanism 10 is finally mounted between a first end cap 12 on an upper side of the rock sample R and a second end cap 14 on a lower side of the rock sample R. These end caps are typically of low mass and made of some low density material. Suitable conventional seals, such as O-rings or the like, are provided at the connections between the end caps 12 and 14 and the jacket member 10 to seal against fluid leakage into the interior of jacket member 10.

The end cap 12 is rigidly connected at a lower end 16 of the spring S. The spring S is in the preferred embodiment a stiff tubular spring member which is rigidly mounted at an upper end 18 to a mounting block 20 fixedly mounted on an upper surface 22 of the test vessel T. As has been set forth, it is desirable during testing to subject the rock sample R to various types of fluids while the sample is subjected to pressure and/or temperature. Accordingly, a fluid system F is provided which delivers fluid to and receives fluid from the rock sample R. An inlet tube 23 which is preferably of a flexible material passes through the interior of the spring S to a supply chamber 24 within the end cap 12 adjacent a first surface 26 of the rock sample R so that a suitable test fluid under a particular desired test pressure may be injected into the jacket member 10. A fluid collection pocket 28 is formed in the end cap 14 so that fluids passing through the rock sample R may pass into a drainage conduit 30 formed in the end cap 14 and therefrom into a return fluid supply line 32. The return fluid supply line 32 passes from the end cap 14 upwardly past the jacket member 10 and through an opening into chamber 24 in end cap 12 and therefrom upwardly through the interior of the spring S and outwardly through the test vessel T.

Excitation of the holding mechanism H may be accomplished either electromagnetically or mechanically. When mechanically, the holding mechanism H is subjected to mechanical vibratory forces. When accomplished electromagnetically, a low mass magnetic body 34 is mounted with the holding mechanism H, at end cap 14 for example. The magnetic body 34 is alternately repelled and attracted by an alternating current magnetic field established by a coil 36 and its associated magnetic core 38. Alternating current power for causing excitation of the coil 36 and corresponding movement of the holding mechanism is provided from an alternating current power supply 40 at a particular frequency, either as a fundamental frequency or harmonic thereof, near the expected frequency of oscillation of the holding mechanism H.

The output frequency from power supply 40 is selected. As has been set forth, in response to excitation on the excitation system E, the holding mechanism H oscillates upwardly and downwardly at a frequency determined by the spring constant k of the spring S and the mass M of the holding mechanism H. The detection system detects the frequency of this oscillation which, once determined, can be used to determine the mass of the rock sample R in the manner set forth above. The detection system D includes a target 42 suitably mounted with the holding mechanism H, such as at the end cap 12. Motion of the target mechanism 42 is detected by the detection system D and the number of times the presence of the target 42 is detected in a particular interval of time indicates the frequency f of oscillation of the holding mechanism H. Detection of the target 42 may be performed optically, magnetically, or acoustically.

In the embodiment shown in the drawings, the target 42 is a low mass magnetic member, the relative motion of which can be sensed by a coil 44 with associated core 46. Coil 44 forms electrical signals due to the relative movement between the magnetic target 42 and the coil 44 which are furnished to a detector circuit 48 which may, for example, be a frequency detector circuit.

As has been set forth, the rock sample R exhibits a frequency response based on its mass m and a spring constant k of the resilient spring R. In evaluating saturation of rock samples, relatively small changes in mass of the rock sample R under different test conditions can be of significant importance. Accordingly, it is often necessary to measure relatively minor changes in mass of the rock sample R. The frequency of the alternating current generator 40 in the excitation system E is selected to be at a frequency near that, if not equal to that, of the expected frequency response of the rock sample R. The detector circuit 48 forms a signal representative of the actual frequency response of the rock sample. A comparator circuit 50 is electrically connected to receive the actual frequency signal from the detector circuit 48 in the detector system D and also the frequency from generator 40 applying the excitation to system E. As an alternative to direct comparison of excitation frequency to the natural frequency of the system, phase differences may also be explored. In this case the phase differences between excitation and response can be used to detect very small changes in system natural frequency. The results obtained in phase comparator 50 may be used to detect small changes in the frequency of vibration of the rock sample R, which are in turn indicative of relatively small changes in saturation of the rock sample R.

The foregoing disclosure and description of the invention are illustrative and explanatory thereof, and various changes in the size, shape and materials, as well as in the details of the illustrated construction may be made without departing from the spirit of the invention.

I claim:

1. An apparatus for determining saturation of a rock sample, while said rock sample is held at conditions of elevated temperature or pressure, said apparatus comprising:
    (a) means for holding said rock sample, said holding means being contained within a test vessel and including means for selectively applying fluid to said rock sample while the rock sample is being held;
    (b) means for applying excitation to said holding means; and
    (c) means for detecting oscillation of said rock sample in response to applied excitation to ascertain the mass of the rock sample and for determining its saturation in accordance with the mass.

2. The apparatus of claim 1, wherein said means for holding comprises:
    resilient spring means for holding the rock sample beneath it.

3. The apparatus of claim 2 wherein:
    said resilient spring means is rigidly mounted on a first end to a support surface forming part of said test vessel.

4. The apparatus of claim 2, wherein said means for holding comprises:
    (a) a first low mass end cap mounted on a first side of the rock sample;
    (b) said first end cap being rigidly mounted to said resilient spring means; and
    (c) a second low mass end cap mounted on an opposite side of the rock sample from said first end cap.

5. The apparatus of claim 4, wherein said means for holding comprises:
    a jacket member extending between said first and second and caps for enclosing the rock sample.

6. The apparatus of claim 1, wherein said means for applying excitation comprises:
   means for applying electromagnetic excitation to said means for holding.

7. The apparatus of claim 6, wherein said means for applying excitation comprises:
   a magnetic body mounted with said means for holding.

8. The apparatus of claim 1, wherein said means for detecting comprises:
   means for magnetically detecting oscillation of the rock sample.

9. The apparatus of claim 1, wherein said means for detecting comprises:
   (a) a target mounted with said means for holding; and
   (b) means for detecting motion of said target.

10. The apparatus of claim 1, wherein said means for detecting comprises:
    means for detecting the frequency of oscillation of the rock sample.

11. The apparatus of claim 10, wherein:
    said resilient spring means is rigidly mounted on a first end to a support surface.

12. The apparatus of claim 1, wherein said means for holding comprises:
    (a) resilient spring means for holding the rock sample beneath it;
    (b) fluid passage means formed in said resilient spring means.

13. The apparatus of claim 12, wherein said means for holding comprises:
    (a) a first end cap mounted on a first side of the rock sample;
    (b) a second end cap mounted on an opposite side of the rock sample from said first end cap;
    (c) fluid passage means formed in each of said end caps communicating with the fluid passage means formed in said resilient spring means.

14. The apparatus of claim 13, wherein said means for holding comprises:
    a jacket member extending between said first and second end caps for enclosing the rock sample.

15. The apparatus of claim 1 wherein said test vessel is a pressure vessel.

16. The apparatus of claim 1 wherein said test vessel is a high temperature oven.

17. a method of determining saturation of a rock sample, while said rock sample is held at conditions of elevated temperature or pressure; comprising the steps of:
    (a) holding the rock sample in a test vessel at elevated temperature or pressure;
    (b) selectively applying fluid to said rock sample;
    (c) applying excitation to the rock sample as it is being held; and
    (d) detecting oscillation of the rock sample in response to the applied excitation to ascertain the mass of the rock sample and thus its saturation.

18. The method of claim 17, wherein said step of holding comprises the step of:
    resiliently supporting the rock sample as it is being held.

19. The method of claim 17, wherein said step of applying excitation comprises:
    applying electromagnetic excitation to the rock sample as it is being held.

20. The method of claim 17, wherein said step of applying excitation comprises:
    applying mechanical excitation to the rock sample as it is being held.

21. The method of claim 17, wherein said step of detecting comprises:
    magnetically detecting oscillation of the rock sample.

22. The method of claim 17, wherein said step of detecting comprises:
    optically detecting oscillation of the rock sample.

23. The method of claim 17, wherein said step of detecting comprises:
    acoustically detecting oscillation of the rock sample.

* * * * *